United States Patent
Hirji

(10) Patent No.: US 7,771,051 B2
(45) Date of Patent: Aug. 10, 2010

(54) NEAR EYE OPTHALMIC DEVICE

(75) Inventor: Rahim Hirji, 3737 Major Mackenzie Drive, Vaughan, ON (CA) L4H 0A2

(73) Assignee: Rahim Hirji, Vaughan, Ontario (CA)

( * ) Notice: Subject to any disclaimer, the term of this patent is extended or adjusted under 35 U.S.C. 154(b) by 263 days.

(21) Appl. No.: 11/768,447

(22) Filed: Jun. 26, 2007

(65) Prior Publication Data

US 2008/0309879 A1 Dec. 18, 2008

Related U.S. Application Data

(63) Continuation-in-part of application No. 11/762,562, filed on Jun. 13, 2007, now abandoned.

(51) Int. Cl.
*A61B 3/02* (2006.01)
*A61B 3/14* (2006.01)
(52) U.S. Cl. .................. 351/223; 351/222; 351/206
(58) Field of Classification Search .......... 351/205–246
See application file for complete search history.

(56) References Cited

U.S. PATENT DOCUMENTS

| 4,807,282 | A |   | 2/1989  | Kazan et al. ............... 379/284 |
| 4,836,670 | A | * | 6/1989  | Hutchinson ............... 351/210 |
| 5,121,981 | A |   | 6/1992  | Waltuck et al. ............ 351/243 |
| 5,416,540 | A | * | 5/1995  | Hayashi .................... 351/239 |
| 5,568,209 | A | * | 10/1996 | Priester et al. ............. 351/243 |
| 5,596,379 | A | * | 1/1997  | Kawesch .................. 351/244 |
| 5,880,814 | A |   | 3/1999  | McKnight et al. .......... 351/244 |
| 6,108,634 | A |   | 8/2000  | Podnar et al. ................ 705/2 |
| 6,578,966 | B2 |   | 6/2003  | Fink et al. ................. 351/239 |
| 7,425,067 | B2 | * | 9/2008  | Warden et al. ............ 351/205 |

* cited by examiner

*Primary Examiner*—Mohammed Hasan
(74) *Attorney, Agent, or Firm*—Bereskin & Parr LLP/S.E.N.C.R.L., s.r.l.

(57) ABSTRACT

The ophthalmic device comprises a memory, display, image data and user input. Image data stored on the memory is used to generate a plurality of visual acuity images. The user input is operable by a user to select selected visual acuity images from the plurality of visual acuity images for display on the display.

16 Claims, 10 Drawing Sheets

NEAR EYE OPTHALMIC DEVICE

RELATED APPLICATIONS

This application is a continuation-in-part of U.S. patent application Ser. No. 11/762,562, filed Jun. 13, 2007 now abandoned, the entire content of which is hereby incorporated by reference.

FIELD OF THE INVENTION

This invention relates to an ophthalmic device in which visual acuity images may be generated, selected and viewed.

BACKGROUND OF THE INVENTION

Optometry practitioners test near visual acuity using a variety of charts printed on paper cards. These cards are typically held by the patient or clipped on to a rod attached to a phoropter.

Some visual acuity tests require that a patient indicate areas of reduced visual acuity on a card. Practitioners can then document approximately which areas on the card are indicated by the patient. This exercise can be repeated during subsequent examinations to monitor the progression of disease.

SUMMARY OF THE INVENTION

In accordance with an aspect of the invention, there is provided an ophthalmic device. The ophthalmic device comprises a memory and a display linked to the memory. The ophthalmic device further comprises image data stored on the memory for generating a plurality of visual acuity images, wherein each visual acuity image in the plurality of visual acuity images is configured to provide diagnostic information for an eye viewing the visual acuity image from up to 28 inches away. The ophthalmic device further comprises a user input operable by a user to select a selected visual acuity image from the plurality of visual acuity images for display on the display; and a processor for retrieving the image data from memory to generate the selected visual acuity image on the display.

BRIEF DESCRIPTION OF THE DRAWINGS

A detailed description of preferred embodiments of the present invention is provided herein below with reference to the drawings, in which.

DETAILED DESCRIPTION OF EMBODIMENTS OF THE INVENTION

Figure 1A:
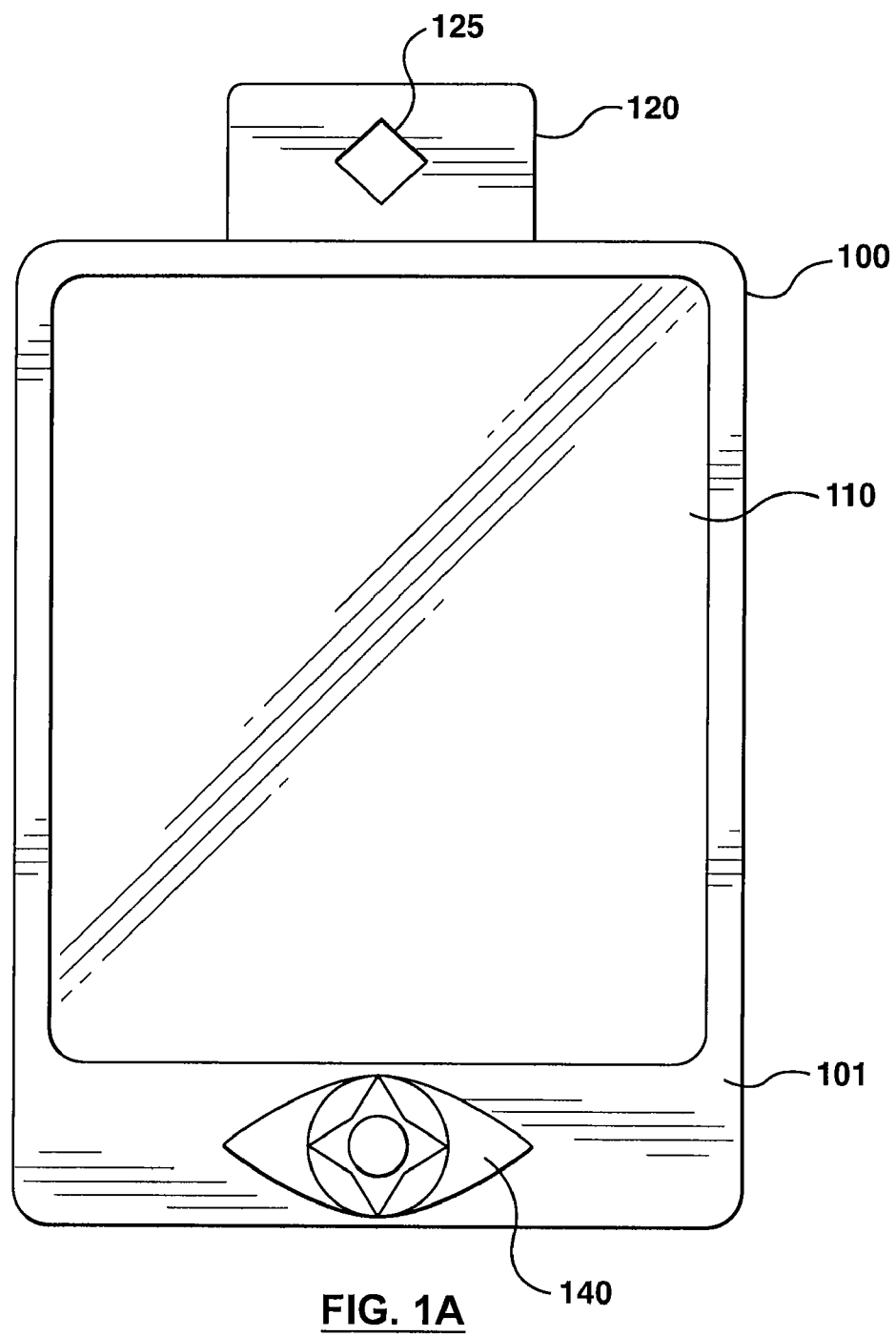
FIG. 1A illustrates, in a front view, an ophthalmic device in accordance with an embodiment of the present invention.

Referring to FIG. 1A, there is illustrated a front view of an ophthalmic device 100 in accordance with an embodiment of the present invention. Ophthalmic device 100 has a housing 101, a display 110, a user input 140 and a coupling 120. The coupling 120 further has a slot 125. Housing 101 is made of a lightweight material, such as injection-molded plastic.

Figure 1B:
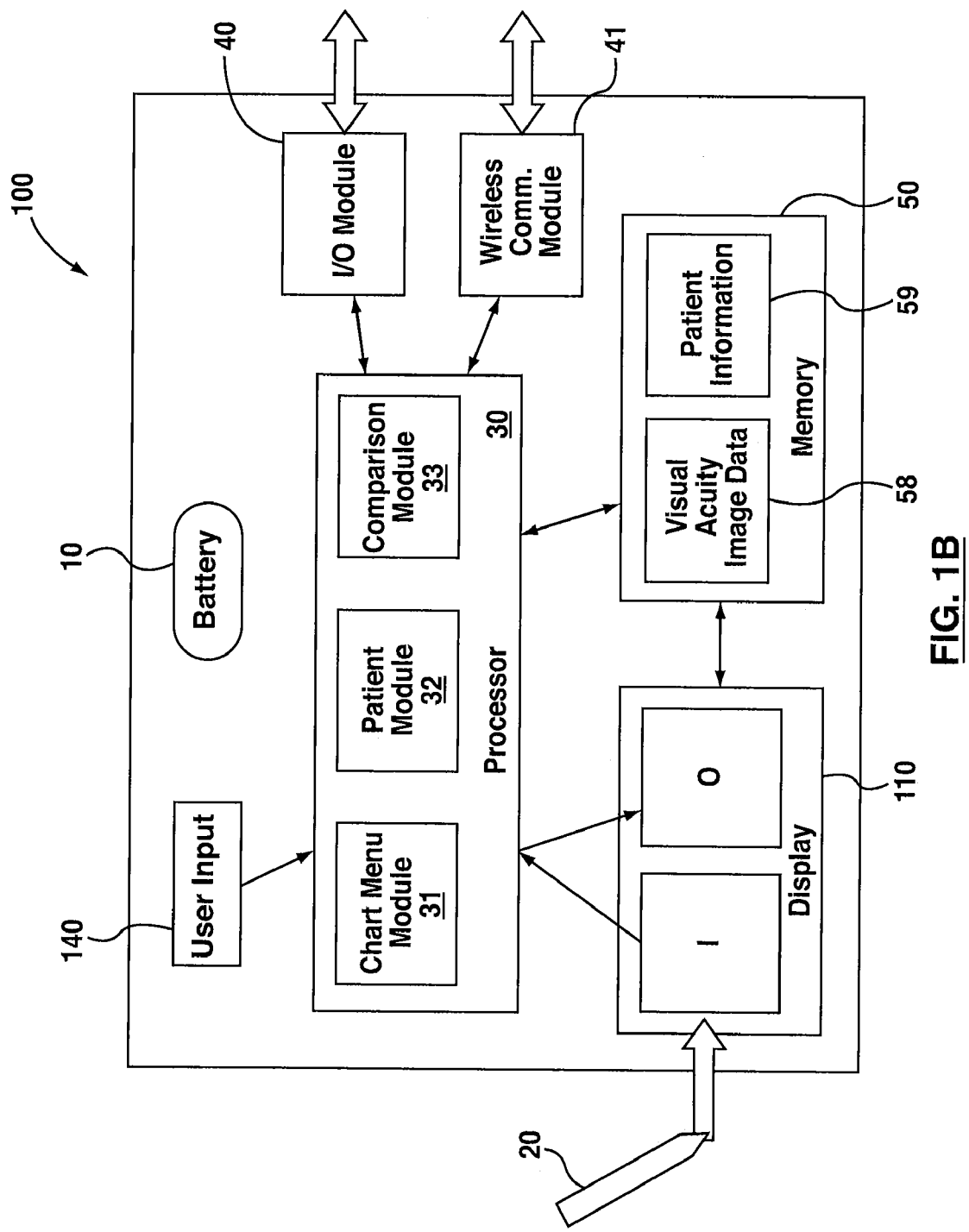
FIG. 1B is a schematic block diagram of the ophthalmic device of FIG. 1A.

Referring now to FIG. 1B, there is illustrated a schematic block diagram of ophthalmic device 100 in accordance with an embodiment of the present invention. Ophthalmic device 100 has a battery 10, a processor 30, input/output (I/O) module 40, memory 50, display 110 and user input 140. In one embodiment, I/O module 40 is a USB interface, providing data transfer capability from the device 100 to a computer for attachment to electronic medical charts. In other embodiments, I/O module 40 is one or more of Bluetooth, remote control infrared communication or flash memory interfaces. Both Bluetooth and remote control infared communication can permit wireless transfer of data from a computer to the device 100 or to a remote control, allowing, in the case of Bluetooth, the device 100 to communicate with other Bluetooth operated instruments. In another embodiment, ophthalmic device 100 has a wireless communication module 41.

Battery 10 is preferably of a lightweight, rechargeable type, such as lithium ion, to enable approximately 8 hours of use between charging. In this case, housing 101 has a connector (not shown) for a power cord or charging cradle, enabling the battery 10 to be charged. In one embodiment, housing 101 has a combined power and data connector, for example to allow battery 10 to be charged while simultaneously transferring data to and from the device memory 50 via I/O module 40 and processor 30.

Display 110 can be a high resolution liquid crystal display (LCD), measuring approximately 4.7" wide by 5.7" high, with a pixel resolution suitable for displaying visual acuity images to facilitate visual acuity diagnosis. For example, to facilitate the use of the device at ranges of, say 16" or less, the display 110 can have a resolution sufficient to clearly display symbols as small as half a millimeter in height, or, potentially even smaller. In other embodiments, display 110 can be of an alternative suitable composition and resolution, such as organic light emitting diode (OLED).

Processor 30 can be configured to operate a chart menu module 31, patient module 32, comparison module 33 and configuration module 34. Each of these modules is described in greater detail below.

Figure 1C:
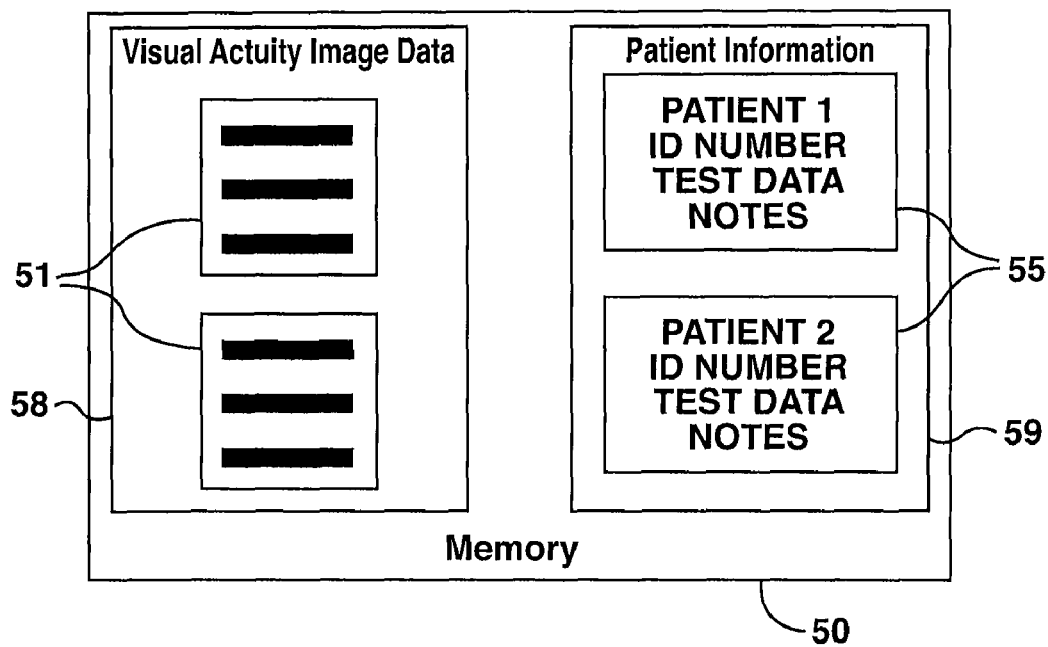
FIG. 1C is a schematic block diagram of a memory of the ophthalmic device of FIG. 1A.

Referring now to FIG. 1C, there is illustrated a schematic view of memory 50 in accordance with an embodiment of the present invention. Memory 50 contains visual acuity image data 58 and patient information data 59. Visual acuity image data 58 consists of a plurality of image data items 51 corresponding to a plurality of visual acuity images. In operation, processor 30 can retrieve one or more image data items 51 from visual acuity image data 58 and generate a corresponding visual acuity image for display on display 110, based on the image data items 51.

Patient information data 59 consists of a plurality of patient data items 55. Patient data items 55 correspond to individual patients and can contain patient information, for example a name, unique identifier, user notes, examination records and visual acuity reference data.

Figure 1D:
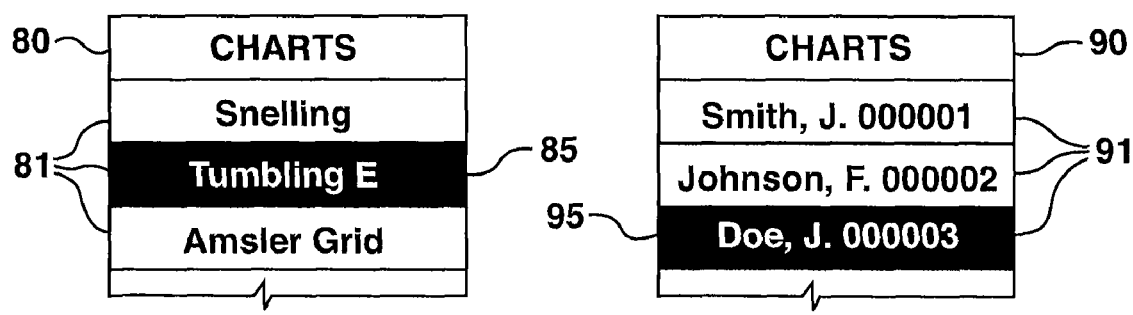
FIG. 1D is a schematic view of selection menus generated for display on the ophthalmic device.

Referring now to FIG. 1D, there is shown a schematic view of selection menus generated for display on ophthalmic device 100. Chart menu module 31 of processor 30 (both shown in FIG. 1B) is configured to retrieve a plurality of image data items 51 from visual acuity image data 58. Each item 51 would typically be the data required to generate a particular chart; however, for simplicity items 51 in FIG. 1C are simply depicted schematically. Chart menu module 31 is configured to operate upon the image data items 51 to generate a chart menu 80 containing a plurality of chart identifiers 81 corresponding to visual acuity image data available in visual acuity image data 58. Processor 30 is further configured to send charts menu 80 for display to a user via display 110. User input 140 is selectively operable by the user to navigate the displayed chart menu 80 to select a visual acuity image by its corresponding chart identifier 81. In operation, a highlighted chart menu item 85 indicates the currently selected chart identifier.

User input 140 consists of directional buttons, and at least one or more selection buttons. In operation, a user uses the directional buttons to scroll through chart menu 80 on display 110. When the desired chart identifier is highlighted on display 110, the user depresses a selection button provided by user input 140 and the corresponding visual acuity image is displayed on display 110. User input 140 further has additional shortcut buttons. One shortcut button is configured to call up chart menu 80. Another shortcut button may be configured to call up a patient menu 90, to select another patient for examination.

Patient module 32 of processor 30 (both shown in FIG. 1B) is configured to retrieve a plurality of patient data items 55 from patient information data 59. Patient module 32 is configured to operate upon the patient data items 55 to generate a patient menu 90 containing a plurality of patient identifiers 91 corresponding to patient data available in patient information data 59. Processor 30 is further configured to send patient menu 90 for display to a user on display 110. User input 140 is selectively operable by the user to navigate the displayed patient menu 90 to select a patient data item 55 by a corresponding patient identifier 91. In operation, a highlighted patient menu item 95 indicates the currently selected patient identifier.

It will be appreciated by those skilled in the art that buttons may perform multiple functions depending on the context of the currently displayed image or menu on display 110.

In one alternative embodiment, there are two housings. A first housing contains a circuit board with a processor, memory, I/O modules, display and a wireless communication module. A second housing contains a user input and a wireless communication module. The user operates the user input to remotely select a visual acuity image for display on the display of the first housing. The wireless communication module enables the sending and receiving of wireless messages between the first and second housing to communicate user input from the second housing to the first housing so that the display of the first housing is updated to display the desired visual acuity image. In one embodiment, the second housing has a second display to enable the user to perceive the currently displayed visual acuity image on the display of the first housing.

In a further alternative embodiment, the first and second housings have couplings enabling the housings to be mated together.

Figure 2:
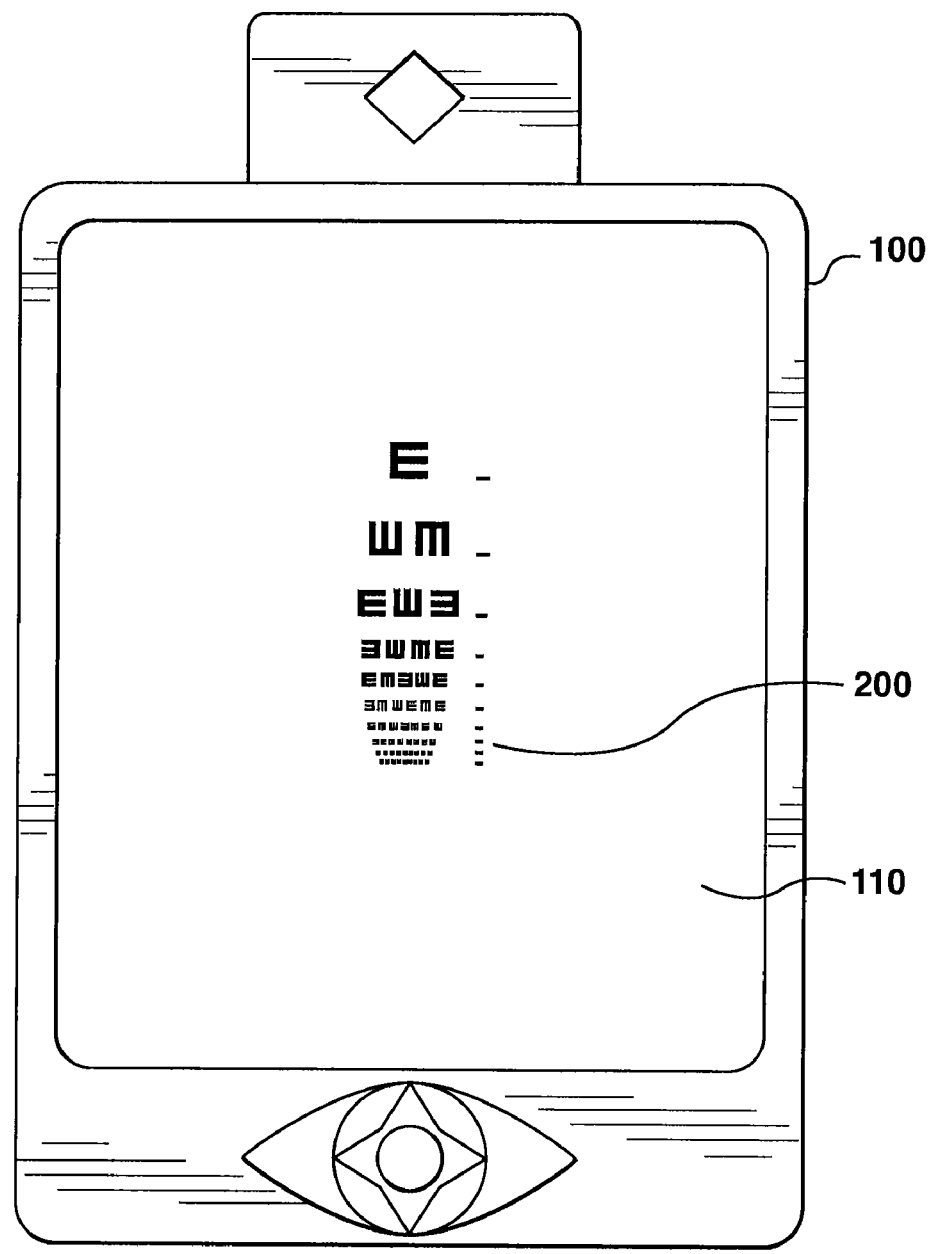
FIG. 2 illustrates, in a front view, the ophthalmic device of FIG. 1A displaying a visual acuity image in accordance with an aspect of the embodiment.
Figure 3:
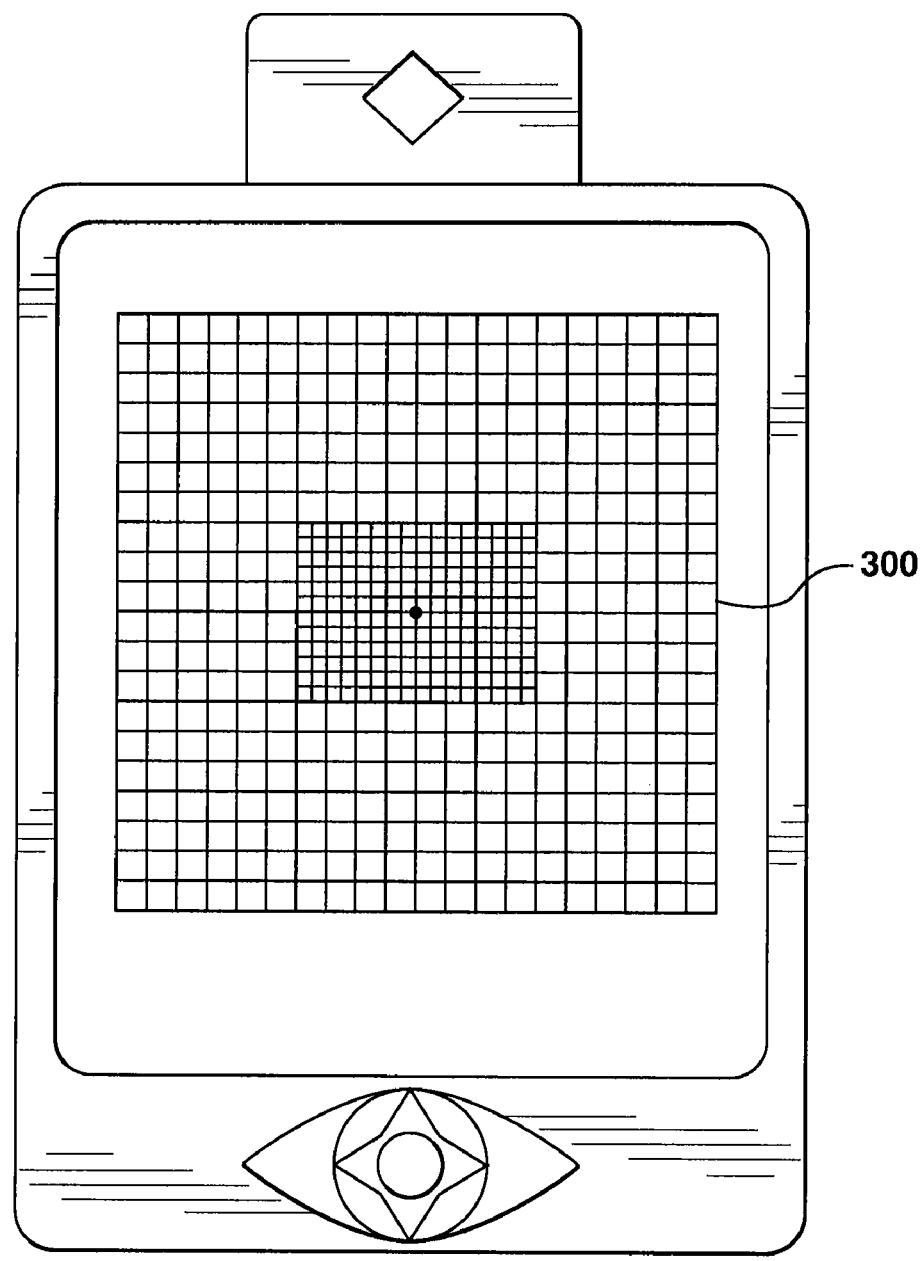
FIG. 3 is a front view of the ophthalmic device of FIG. 1A displaying an alternative visual acuity image in accordance with another aspect of the embodiment.

Referring now to FIGS. 2 and 3, there are illustrated front views of ophthalmic device 100 in accordance with an embodiment of the present invention. In FIG. 2, display 110 is displaying a selected visual acuity image 200 from a plurality of visual acuity images generated by ophthalmic device 100 from image data stored on memory 50. The visual acuity image 200 is configured to provide diagnostic information related to visual acuity. In FIG. 2, visual acuity image 200 is a chart with different orientations of the letter E in decreasing sizes, also known as a "Tumbling E" chart, which is commonly used when measuring visual acuity in pediatric, illiterate, non-English speaking or non-verbal patients. In FIG. 3, display 110 is displaying another selected visual acuity image 300 from a plurality of visual acuity images generated by ophthalmic device 100 from image data stored on memory 50. In FIG. 3, visual acuity image 300 is configured to provide diagnostic information related to age related macular degeneration and consists of a vertical and horizontal grid with a centrally disposed solid dot. The visual acuity image 300 illustrated in FIG. 3 is also known as an "Amsler Grid". If a patient indicates that they cannot perceive certain grid boxes, this is indicative of scotoma. If a patient indicates that lines are distorted, this is indicative of metamorphopsia.

Ophthalmic device 100 may be configured to generate other visual acuity images corresponding to standardized charts containing symbols of different sizes with associated measurement indicators for indicating the level of visual acuity required to perceive said symbols at a predefined distance of up to 28" away. Example of such visual acuity images include: 1) a letter chart with lines of alphabetic characters oriented such that the largest sized characters are placed at the top of the chart and each successive line below has smaller sized characters, otherwise known as a Snellen chart or its equivalent; 2) a letter chart with an equal number of letters on any given line and a logarithmic progress of line spacing, otherwise known as an ETDRS near chart; 3) a pictographical chart with familiar picture symbols such as a house or apple, useful to measure visual acuity in children and otherwise known as Lea or picture symbol charts; 4) a letter chart with large sized letters designated in the M system, such as 1M equaling to 20/50 Snellen equivalent; 5) a chart with different orientations of the letter C, otherwise known as the Landolt C test; 6) a number chart, useful for patients who can identify and relate to numbers; and 6) Von Graefe phoria test, fused cross cylinder, monocular cross cylinder, low vision, Hart chart test or other vision therapy test chart. It will be appreciated by those skilled in the art that still other visual acuity images suitable for visual acuity testing may be generated.

User input 140 is selectably operable by the user using chart menu 80 to select from a plurality of visual acuity images for display on display 110. Chart menu 80 can be further configured to enable the user to select using user input 140 a desired visual acuity metric for use with the selected visual acuity image from a list of visual acuity metrics. For example, the visual acuity metric can be a Snellen value, a J system value, a LogMAR value or other suitable value. In operation, the user selects a chart from chart menu 80 using user input 140. By default, a visual acuity image is generated with predetermined visual acuity metrics corresponding to each symbol or set of symbols. For example, a Snellen chart is generated by default with Snellen values displayed corresponding to each line of the chart. Optionally, the user can select a different visual acuity metric to display in place of, or in addition to, the default metric. For example, the user may choose to display LogMAR equivalent metrics on a Snellen chart.

User input 140 can be further configured to select a configuration mode, controlled by configuration module 34 (shown in FIG. 1*b*). Configuration module 34 can be configured to 1) calibrate ophthalmic device 100 for operation at a desired distance from the patient; 2) change viewing characteristics of display 110; and 3) reconfigure visual acuity images.

In operation, user input 140 can be operable by the user to enter a configuration mode controlled by configuration module 34. User input 140 can be further operable to initiate a distance calibration of ophthalmic device 100. By default, ophthalmic device can be configured to generate visual acuity images calibrated for viewing at a distance of 16 inches. This calibration is based on the physical size and resolution of display 110. If desired, a user is able to measure the distance between a patient and ophthalmic device 100 and provide this measurement to ophthalmic device 100 using user input 140. Configuration module 34 is configured to accept the provided distance measurement and calculate a corresponding correct size at which to generate visual acuity images, based on the physical size and resolution of display 110. For example, for a Snellen Chart visual acuity image, there is a reference height for a "20/20" letter on the chart, when viewing the letter from a predetermined distance. The reference height is determined by a trigonometric relationship given by twice the distance between the eye and the letter on a chart along the line of sight multiplied by the tangent of 2.5 minutes of arc, or $2d \cdot \tan(0.4167°)$ where d is the distance and $0.4167°$ is the equivalent of 2.5 minutes of arc expressed in degrees. Thus, at a distance of 20 feet (6,096 millimeters), the reference height of a "20/20" letter is 0.349 inches (8.87 millimeters). When the visual acuity image is placed closer to the patient, for example at a distance of 16 inches (406.4 millimeters), the reference height of a "20/20" letter is 0.023 inches (0.59 millimeters). Montgomery, Ted M. describes the derivation of this formula in "Anatomy, Physiology and Pathology of the Human Eye" (http://www.tedmontgomery.com/the_eye/acuity.html), the content of which is incorporated by reference in the present application.

Configuration module 34 can be further operable to allow a user to change viewing characteristics of display 110, using user input 140. For example, if desired, a user can adjust the brightness, contrast and background characteristics of display 110.

Configuration module 34 can be further operable to allow a user to reconfigure visual acuity images using user input 140 for display on display 110. For example, the user can operate user input 140 to highlight or isolate individual letters or symbols in a displayed visual acuity image. A patient can be instructed to identify a particular highlighted letter or symbol. Alternatively, the user can reposition the highlighted letter or symbol relative to other letters or symbols in the displayed visual acuity image. Alternatively, the user can selectively operably change the displayed letter or symbol. Using user input 140, the user can also adjust the number of lines of differing size to be displayed in a visual acuity image, the spacing of the lines, the number of letters or symbols to be displayed in a visual acuity image, and the spacing of the letters or symbols. Alternatively, user input 140 is operable to select a randomization function of configuration module 34, whereby a desired type of visual acuity image is generated with a random selection and ordering of letters or symbols suitable for the desired type of visual acuity image. For example, in the case where the user is concerned that the patient may have memorized the particular line of letters or symbols, the user can operate the user input to randomize particular lines such that different symbols of the same size replace the symbols previously shown. A user might, for example, randomize a given line, or particular symbol on a given line, by first isolating that line or symbol as described above using the user input 140, and then invoking the randomized function.

In alternative embodiments with a second housing containing a wireless communication module and user input, the user input can be configured to remotely operate configuration module 34.

Figure 4:
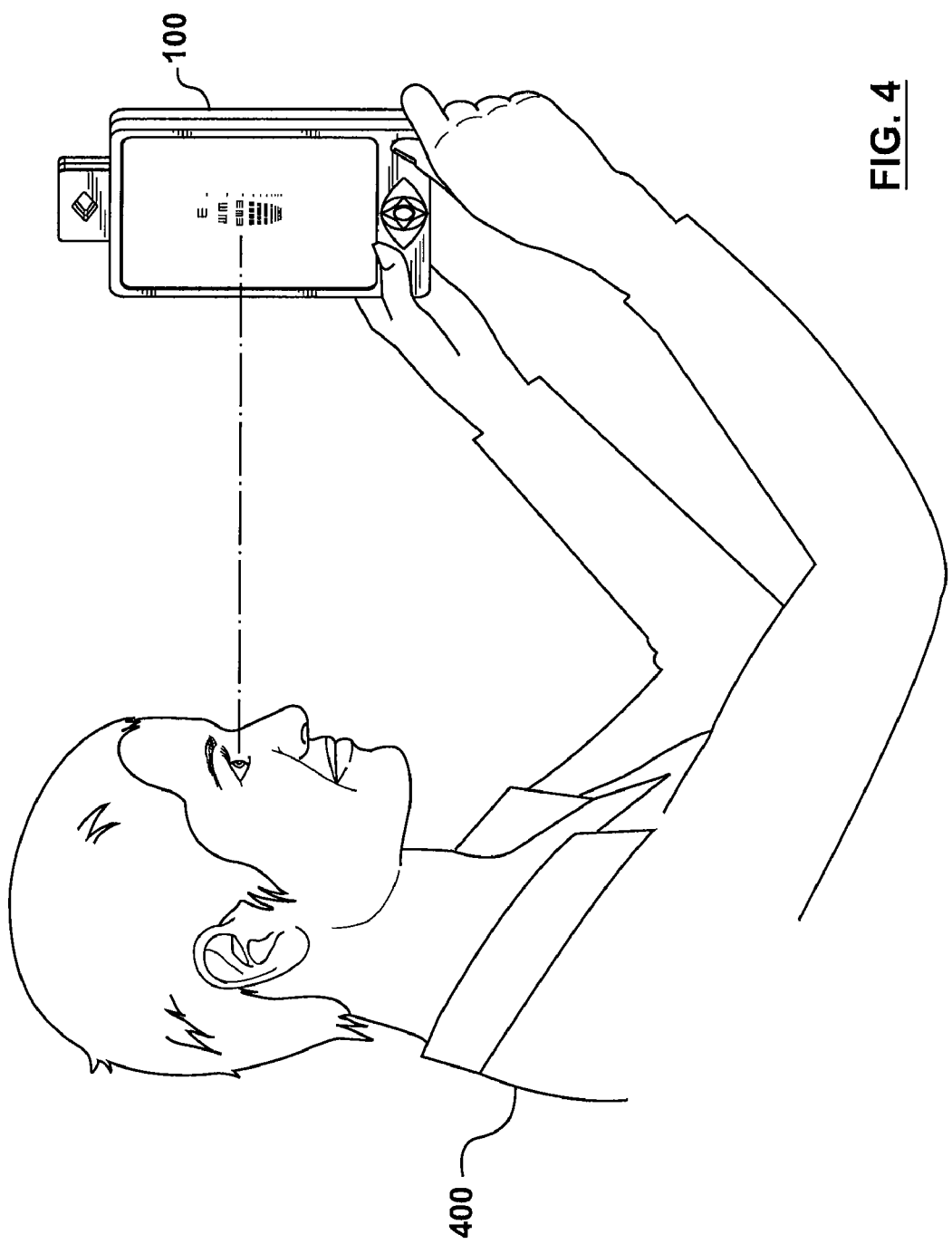
FIG. 4 is a perspective view of the ophthalmic device of FIG. 1A being held by a patient in accordance with an aspect of the embodiment.

Referring now to FIG. 4, there is shown a perspective view of a patient 400 holding ophthalmic device 100. Ophthalmic device 100 is lightweight and small enough that a patient can comfortably hold the device at eye level at a predetermined horizontal distance up to and including arm's length for the duration of a test period. In the preferred embodiment, ophthalmic device 100 weighs less than 4 lbs and measures approximately 5.4"×6.8"×1" (width×height×depth).

Figure 5:
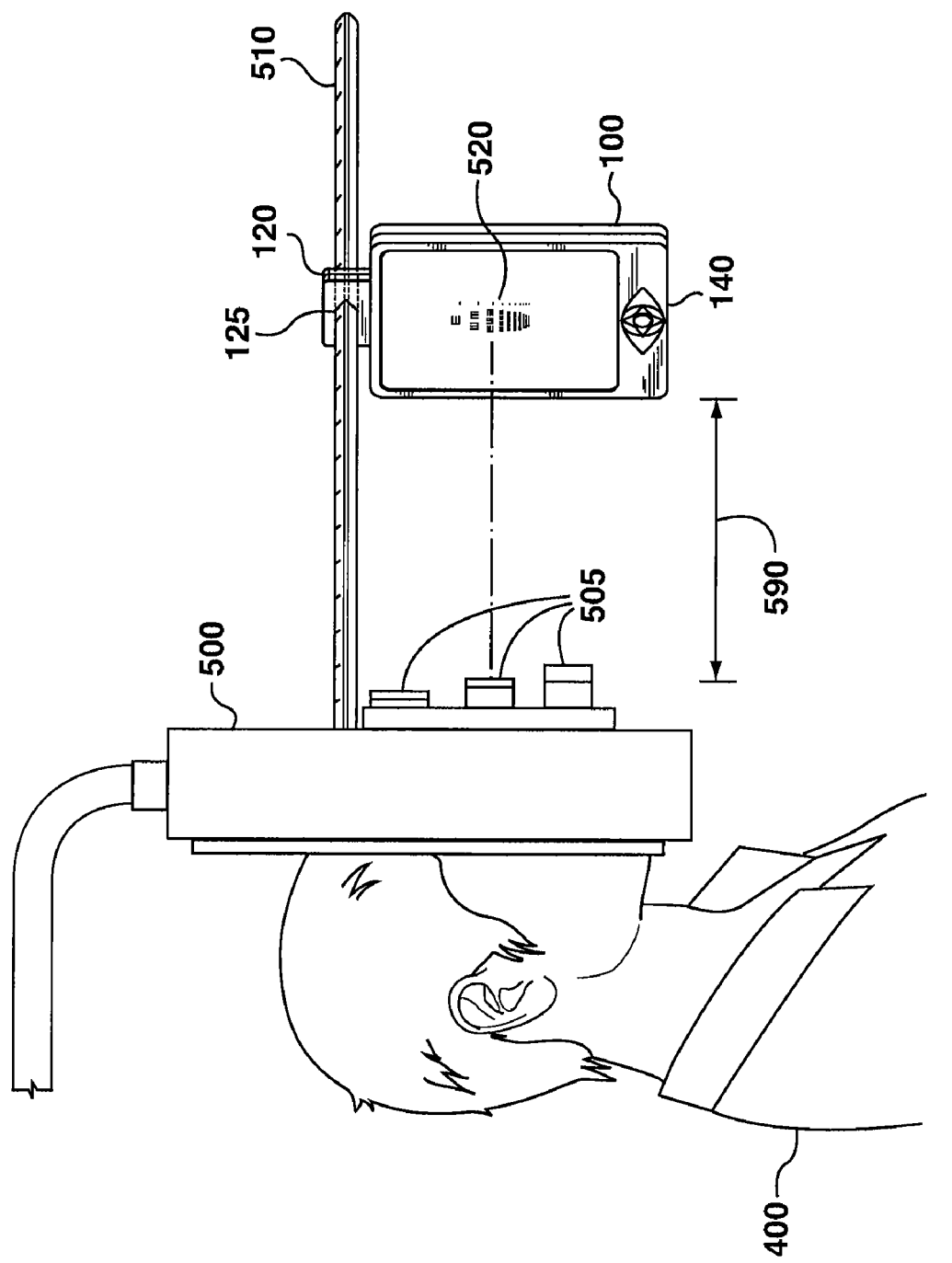
FIG. 5 is a perspective view of the ophthalmic device of FIG. 1A mounted on a support structure in accordance with an aspect of the embodiment.

Referring now to FIG. 5, there is shown a perspective view of patient 400 viewing through a phoropter 500 a selected visual acuity image 520 from a plurality of visual acuity images generated by ophthalmic device 100. Ophthalmic device 100 is lightweight so that it may be coupled to a phoropter rod 510 via slot 125 of coupling 120. Furthermore, ophthalmic device 100 may be movably positioned at a predetermined horizontal distance 590 from phoropter 500. In one embodiment, the predetermined horizontal distance is approximately 16". In other embodiments, the predetermined horizontal distance is up to 28".

Figure 6:
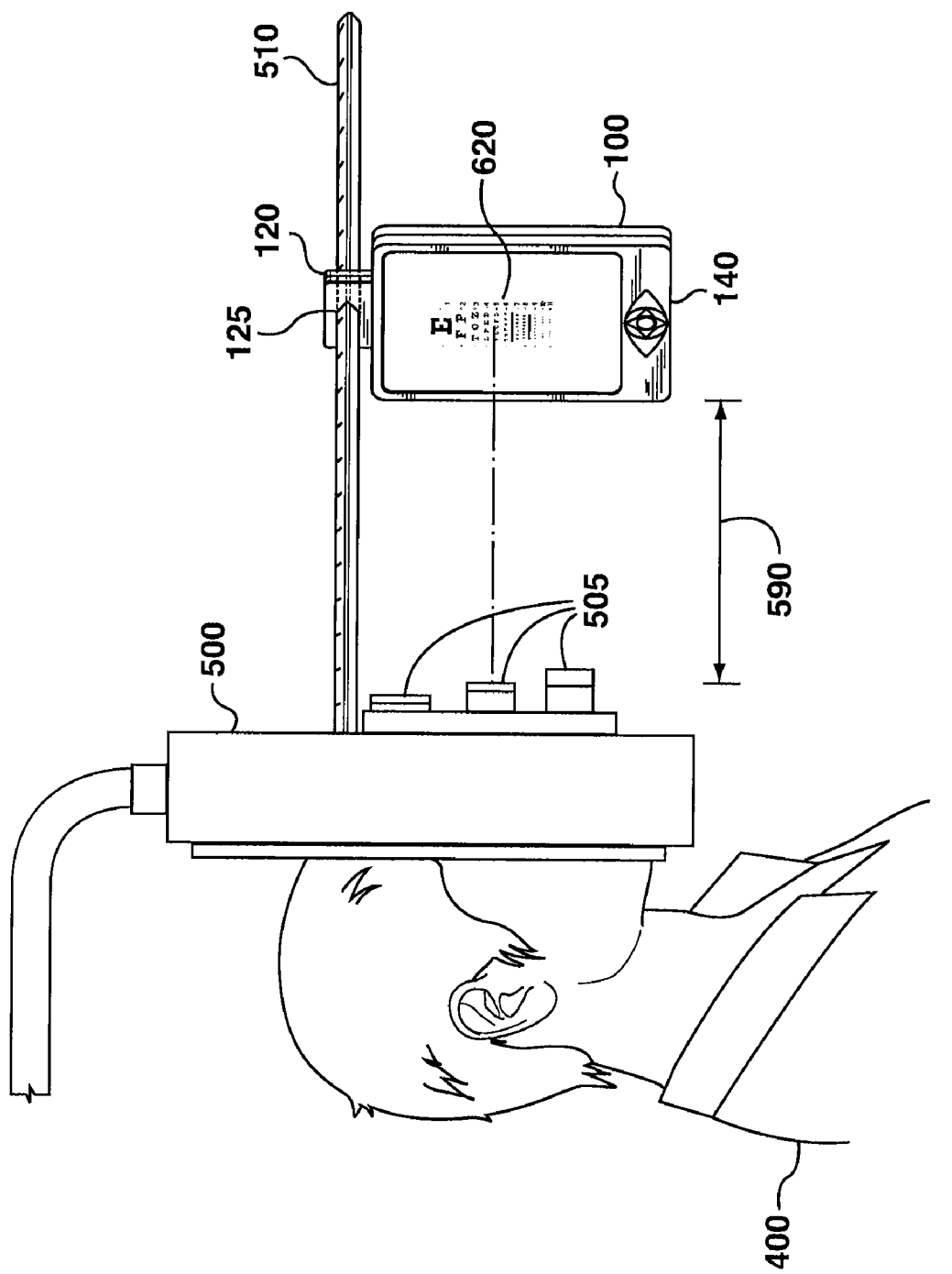
FIG. 6 is a perspective view of the ophthalmic device of FIG. 1A mounted on a support structure in accordance with an aspect of the embodiment.

Referring now to FIG. 6, there is shown a perspective view of patient 400 viewing through a phoropter 500 another selected visual acuity image 620 from a plurality of visual acuity images generated by ophthalmic device 100. User input 140 is operable by a user using chart menu 80 to selectively choose a visual acuity image from the plurality of visual acuity images generated by ophthalmic device 100. Patient 400 remains positioned at phoropter 500 and predetermined horizontal distance 590 remains unchanged while the user (the optometrist) chooses multiple visual acuity images from the plurality of visual acuity images generated by ophthalmic device 100 with patient 400 providing responses to each successive selected visual acuity image until an optometric diagnosis is made.

Figure 7:
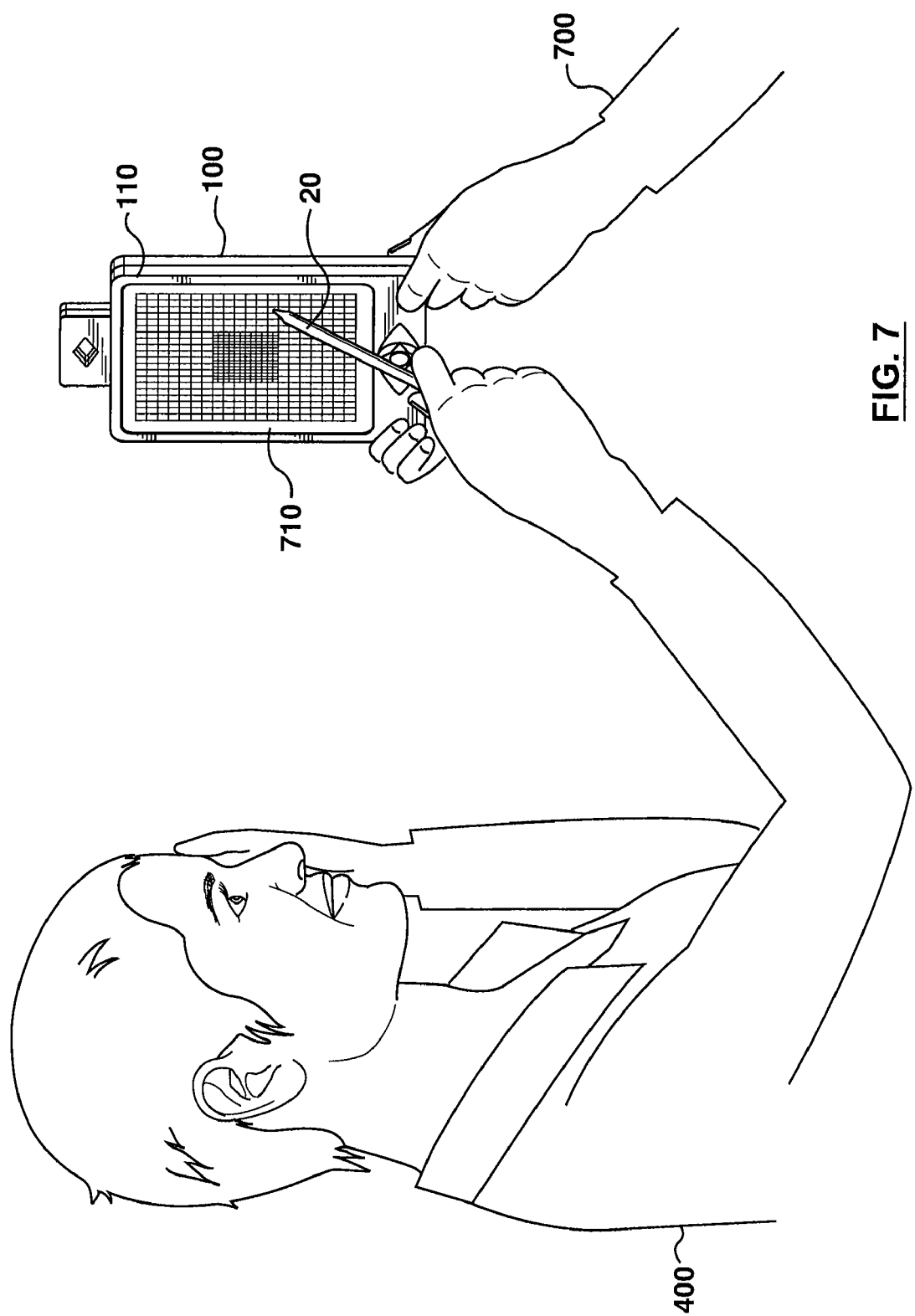
FIG. 7 is a perspective view of the ophthalmic device of FIG. 1A being held by a user and accepting input from a patient in accordance with an aspect of the embodiment.

Referring now to FIG. 7, there is shown a perspective view of patient 400 indicating with a patient input 20 areas of reduced visual acuity on visual acuity image 710, which has been selected from a plurality of visual acuity images generated by ophthalmic device 100. Selected visual acuity image 710 is an Amsler grid. Ophthalmic device 100 is held by a user 700. Patient 400 is instructed to cover one eye using one hand. Alternatively, patient 400 can be instructed to cover one eye using an occluder. In the other hand, patient 400 holds patient input 20, for example a stylus pen. Display 110 of ophthalmic device 100 can be a touch-sensitive display configured to receive input from patient input. Patient 400 can touch display 110 using patient input 20 at areas where the patient perceives aberrations in the grid pattern, such as missing grid boxes or distorted lines. In the case of missing grid boxes or distorted lines, patient 400 can use patient input 20 to draw the approximate size and location the impairments. Ophthalmic device 100 detects the input on display 110 and stores the indicated areas and their relation to the grid pattern along with corresponding patient data items 55 in memory 50. Ophthalmic device 100 is further configured to generate a marked Amsler grid image with markings indicating the areas of reduced visual acuity indicated by the patient. In one embodiment, patient input 20 is a digital stylus pen. In another embodiment, patient input 20 is a finger of patient 400. In yet another embodiment, patient input 20 is held and used by user 700 in response to instructions from patient 400.

In one embodiment, housing 101 of ophthalmic device 100 has a fastener (not shown) for stowing patient input 20 when not in use. The fastener is located on the surface of the housing, for example on the side, such that patient input 20 can be conveniently attached to and detached from the housing 101. The fastener can be a magnet, Velcro, clip, or any other suitable fastener as will be known to those skilled in the art. In an alternative embodiment, housing 101 of ophthalmic device 100 has a cavity adapted to removably accept patient input 20.

The above exercise can be repeated during subsequent patient examinations. Thus, over the course of multiple examinations, a series of patient-indicated areas of reduced visual acuity is compiled, allowing the progression of macular degeneration to be tracked. User input 140 is operable to selectively recall the patient's prior marked Amsler grid images using patient module 32 and patient menu 90. In one embodiment, a comparison module 33 can be configured to perform a comparison of a series of patient Amsler grids stored in the corresponding patient data items 55 in memory 50 and generate a graphical representation of the progression of the patient's disease. This representation can be a color-coded image, with a color gradient corresponding to the age of areas of reduced visual acuity. Alternatively, the representation can be a time-lapse series of images or video, showing the progression of the patient's disease.

Figure 8A:
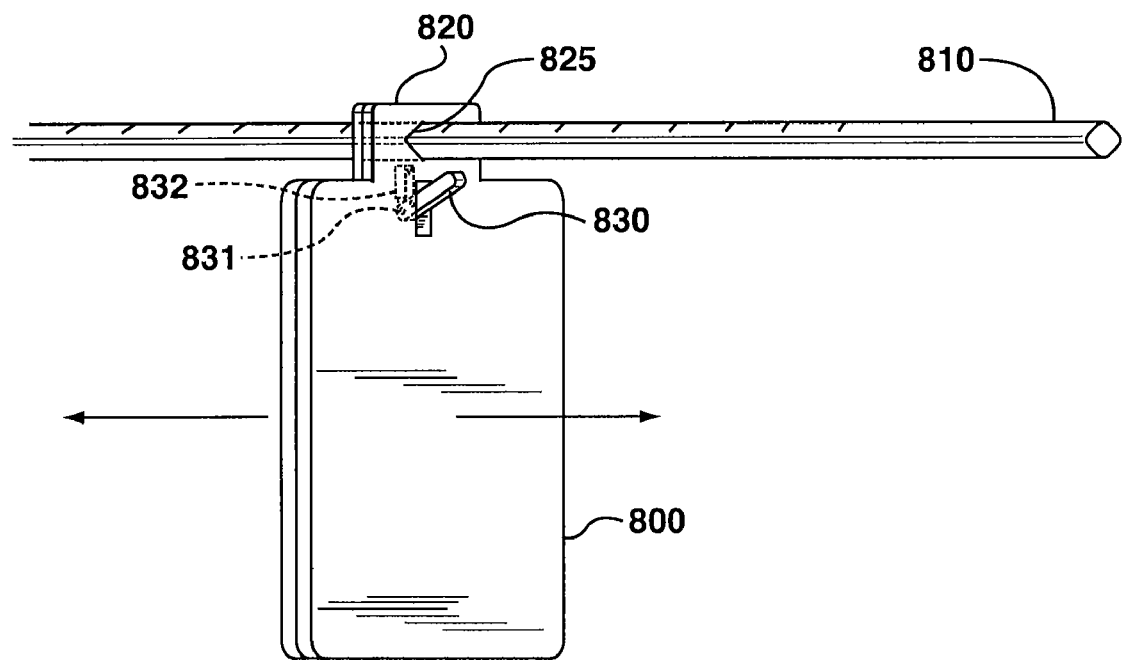
FIGS. 8A and 8B are perspective cut-away views of a lock in accordance with an aspect of an embodiment of the present invention.
Figure 8B:
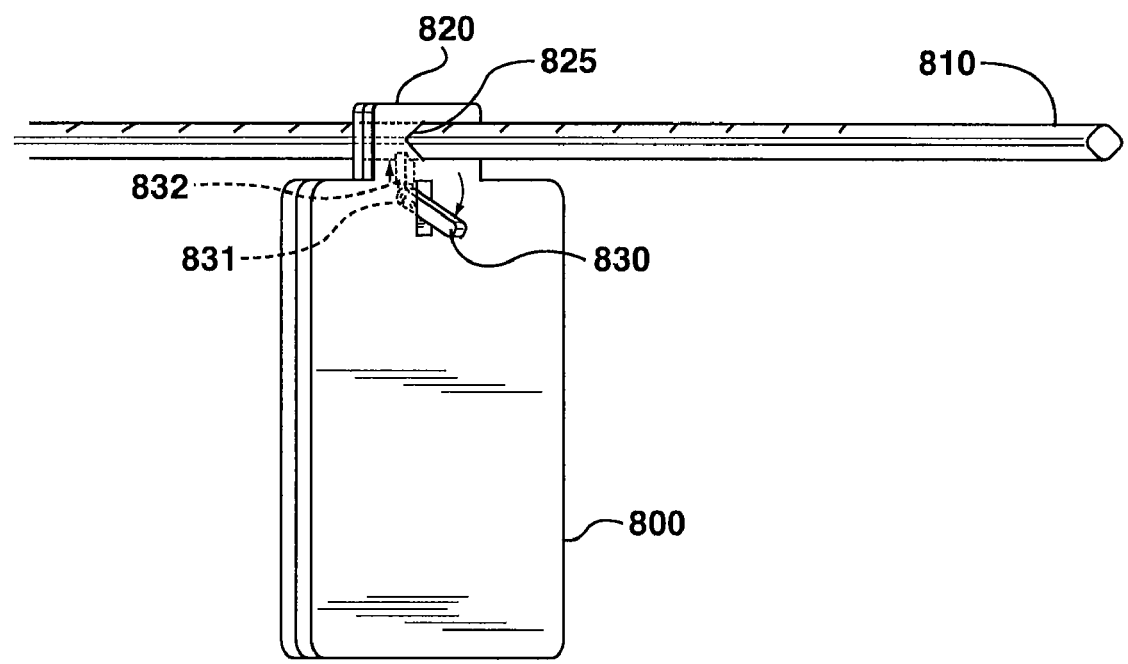

Referring now to FIGS. 8A and 8B, there are shown perspective cut-away views of a lock 830. An ophthalmic device 800 in accordance with an embodiment of the invention is positioned on a support structure 810 via coupling 820. Coupling 820 has a slot 825 for mating to the support structure 810. Ophthalmic device 800 has a hinged actuator 830 mounted beneath coupling 820. Hinged actuator 830 has a hinge 831 and attached stop 832. In a dynamic mode, hinged actuator is in the "unlocked" position, such that stop 832 is not engaged with support structure 810 and therefore ophthalmic device 800 may be freely, slidably positioned on said structure. In a static mode, hinged actuator is in the "locked" position, such that stop 832 is upwardly engaged with support structure 810, thus preventing ophthalmic device 800 from slidably moving along said structure. In one embodiment, support structure 810 has a series of notches at regular intervals corresponding in size to stop 832, such that stop 832 fits into said notches. In another embodiment, support structure has a continuous surface and stop 832 is made of a soft, high-friction material, for example rubber, such that stop 832 acts as a brake. In other embodiments, lock 830 may be oriented above or to the side of support structure 810.

In one alternative embodiment, coupling 820 is removably and attachably disposed on ophthalmic device 800, enabling the display and user input portion to be detached from coupling 820 without removing the coupling from support structure 810. In another alternative embodiment, coupling 820 is pivotally movably mounted on ophthalmic device 800, such that the display portion may be pivoted up and down or side to side, while remaining attached to support structure 810.

In another alternative embodiment, ophthalmic device 100 is provided with an audio output and an audio module. The audio module is configured to retrieve language preferences from patient information data for a particular patient and further retrieve digital audio files corresponding to the patient's language preferences from memory 50. Audio module is further configured to play the digital audio files to the patient via the audio output. In this way, patients can receive instructions for carrying out visual acuity testing in a language familiar to them. For example, in the case where an Italian speaking patient is viewing an Amsler Grid, audio instructions in Italian could tell the patient to indicate the display grid boxes that they can not perceive, or lines that appear to be distorted.

In the case of patients whose language skills are fairly minimal, an audio output could instruct them to agree or disagree with respect to a particular symbol. For example, in the case of a small child, the child could be asked if a particular symbol shown was, say, a star. Then the child could answer either yes or no.

In a further alternative embodiment, ophthalmic device 100 is provided with a digital camera. The digital camera is operable by a user to photograph lesions of the external ocular area. Digital images can be stored with corresponding patient data items 55 in memory 50. Subsequently, the user can transfer the digital images to another computer using I/O module 40.

The present invention has been described here by way of example only. Various modifications and variations may be made to these exemplary embodiments without departing from the spirit and scope of the invention, which is limited only by the appended claims.

The invention claimed is:

1. An ophthalmic device comprising a memory; a display linked to the memory; image data stored on the memory for generating a plurality of visual acuity images, wherein each visual acuity image in the plurality of visual acuity images is configured to provide diagnostic information for an eye viewing the visual acuity image from up to 28 inches away; a user input operable by a user to select a selected visual acuity image from the plurality of visual acuity images for display on the display; and a processor for retrieving the image data from memory to generate the selected visual acuity image on the display, and the device has a weight of under 4 lbs.

2. The device of claim 1, wherein the plurality of visual acuity images are plurality of standardized visual acuity testing charts comprising at least one of a Snellen Chart, an ETDRS Near Chart, a Tumbling E Chart, a Lea Chart, a Picture Symbol Chart, a Low Vision Chart, an Amsler grid Chart, a Number Chart, A Von Graefe Phoria Test, a Fused Cross Cylinder Test, a Monocular Cross Cylinder Test, a Vision Therapy Test Chart, a Hart Chart and a Landolt C test chart.

3. The device as defined in claim 2 wherein the display is further operable to display a chart menu listing a plurality of chart identifiers, wherein for each chart in the plurality of standardized visual acuity testing charts, the user input is operable by the user to select the chart by selecting a corresponding chart identifier in the plurality of chart identifiers.

4. The device as defined in claim 2, wherein the memory and the display are contained in a first housing, and the user input is contained in a second housing separate from the first housing, the device further comprising a wireless communication module for sending and receiving wireless messages between the first housing and the second housing.

5. The device as defined in claim 4 wherein the second housing comprises an input display for displaying a chart menu listing a plurality of chart identifiers, wherein for each chart in the plurality of standardized visual acuity testing charts, the user input is operable by the user to select the chart by selecting a corresponding chart identifier in the plurality of chart identifiers.

6. The device as defined in claim 2 wherein the user input is operable by the user to calibrate the displayed size of visual acuity testing charts based on a line-of-sight distance of the device from a patient.

7. The device as defined in claim 2 wherein the user input is operable by the user to randomize symbols in the visual acuity testing charts.

8. The device of claim 1, further comprising a patient input operable by a patient viewing the selected visual acuity image on the display to indicate an area of impaired visual acuity, wherein the memory is operable to store the area of impaired visual acuity.

9. The device of claim 8, wherein the selected visual acuity image is an Amsler Grid, and the memory is operable to store at least one selected area of the Amsler Grid, selected by the patient using the patient input.

10. The device of claim 8 wherein the user input is operable by the user to enter a patient identifier for identifying the patient and the memory is operable to store the area of impaired visual acuity in association with the patient identifier for the patient.

11. The device of claim 1 further comprising a coupling for mounting the device on a support structure, wherein the coupling is selectably operable to release the device from the support structure.

12. The device of claim 11, wherein the support structure is a phoropter rod, for measuring a distance of the coupling from a phoropter.

13. The device of claim 11, wherein the coupling comprises a lock for switching between a static mode and a dynamic mode, wherein in the static mode, the coupling is secured at a point along the length of the support structure, and in the dynamic mode the coupling is movable along the support structure.

14. The device of claim 13, wherein the support structure is a phoropter rod.

15. The device as defined in claim 1 wherein the display is a high resolution LCD.

16. The device as claimed in claim 1 wherein each visual acuity image in the plurality of visual acuity images comprises i) a plurality of sets of symbols of different sizes, and ii) for each set of symbols in the plurality of sets of symbols, a visual acuity indicator for indicating an associated visual acuity measure when the set of symbols is seen by the eye viewing the symbol from a predefined distance of up to 28 inches away.

* * * * *